United States Patent [19]

Chester et al.

[11] Patent Number: 4,618,737

[45] Date of Patent: Oct. 21, 1986

[54] PEROXIDE-INDUCED POLYMERIZATION OF MOGD LIQUIDS TO HIGH VISCOSITY LUBES

[75] Inventors: Arthur W. Chester, Cherry Hill; William E. Garwood, Haddonfield; Samuel A. Tabak, Wenonah, all of N.J.

[73] Assignee: Mobil Oil Corporation, New York, N.Y.

[21] Appl. No.: 808,705

[22] Filed: Dec. 13, 1985

[51] Int. Cl.$^4$ ................................................. C07C 2/02
[52] U.S. Cl. ..................................... 585/329; 585/330; 585/517; 585/520; 585/533
[58] Field of Search ............... 585/329, 330, 517, 518, 585/521, 533, 520

[56] References Cited

U.S. PATENT DOCUMENTS

| | | | |
|---|---|---|---|
| 4,520,221 | 5/1985 | Hsia Chen | 585/517 |
| 4,524,232 | 6/1985 | Chester et al. | 585/517 |
| 4,547,609 | 10/1985 | Dessau | 585/517 |
| 4,568,786 | 2/1986 | Hsia Chen et al. | 585/517 |

Primary Examiner—Asok Pal
Attorney, Agent, or Firm—A. J. McKillop; M. G. Gilman; L. G. Wise

[57] ABSTRACT

High viscosity lubricants are formed by oligomerizing olefins in two stages. The first stage converts a lower olefin feed to distillate range hydrocarbons in the presence of an aluminosilicate zeolite such as ZSM-5. The distillate effluent from the first stage is further polymerized to lubricant range hydrocarbons at elevated temperatures in the presence of a ditertiary alkylperoxide catalyst.

15 Claims, No Drawings

PEROXIDE-INDUCED POLYMERIZATION OF MOGD LIQUIDS TO HIGH VISCOSITY LUBES

FIELD OF THE INVENTION

This invention relates to the manufacture of lubricating oils (lubes). In particular, this invention provides for a process for the manufacture of lubricating oils by the multi-stage conversion (oligomerization) of olefins. Conversion in each stage takes place in the presence of a certain class of catalyst.

BACKGROUND OF THE INVENTION

Recent work in the field of olefin upgrading has resulted in a catalytic process for converting lower olefins to heaver hydrocarbons. Heavy distillate and lubricant range hydrocarbons can be synthesized over ZSM-5 type catalysts at elevated temperatures and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank, and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. Particular interest is shown in a technique developed by Garwood, et al, as disclosed in European Patent Appication No. 83301391.5, published Sept. 29, 1983. In U.S. Pat. Nos. 4,150,062; 4,211,640 and 4,227,992 Garwood et al disclose the operating conditions for the Mobil Olefin to Gasoline/Distillate (MOGD) process for selective conversion of $C_3+$ olefins to mainly aliphatic hydrocarbons.

In the process for catalytic conversion of olefins to heavier hydrocarbons by catalytic oligomerization using a medium pore shape selective acid crystalline zeolite, such as ZSM-5 type catalyst, process conditions can be varied to favor the formation of hydrocarbons of varying molecular weight. At moderate temperature and relatively high pressure, the conversion conditions favor $C_{10}+$ aliphatic product. Lower olefinic feedstocks containing $C_2$-$C_8$ alkenes may be converted; however, the distillate mode conditions do not convert a major fraction of ethylene. A typical reactive feedstock consists essentially of $C_3$-$C_6$ mono-olefins, with varying amounts of nonreactive paraffins and the like being acceptable components.

The above-described shape-selective oligomerization, as it applies to the conversion of $C_2$-$C_{10}$ olefins over ZSM-5, is known to produce higher olefins up to $C_{30}$ and higher. As reported by Garwood in Intrazeolite Chemistry 23, (Amer. Chem. Soc., 1983), reaction conditions favoring higher molecular weight product are low temperature (200°-260° C.) (390°-500° F.), elevated pressure (about 2000 kPa or greater), and long contact time (less than 1 WHSV). The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of ZSM-5 type catalysts impose shape-selective constraints on the configuration of the large molecules, accounting for the differences with other catalysts.

The following model reaction path for propylene is set forth for purposes of explanation, and it should be taken as a theoretical path, as the process is presently understood by workers in the field.

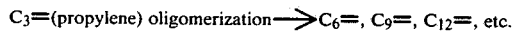

($C_3$ oligomers);

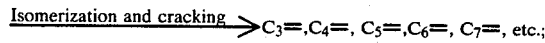

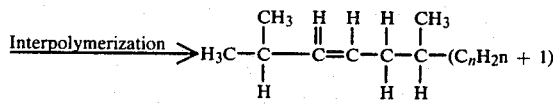

(representative structure).

The desired oligomerization-polymerization products include $C_{10}+$ substantially linear aliphatic hydrocarbons. The ZSM-5 catalytic path for propylene feed provides a long chain with approximately one lower alkyl (e.g., methyl) substituent per 5 or more carbon atoms in the straight chain. The lubricant range final product can be depicted as a typical linear molecule having a sparingly-sutstituted (saturated) long carbon chain, as follows:

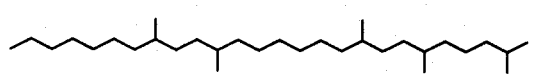

The final molecular conformation is influenced by the pore structure of the catalyst. For the higher carbon numbers, the structure is primarily a methyl-branched straight olefinic chain, with the maximum cross section of the chain limited by the pore size constraints of ZSM-5. Although emphasis is placed on the normal 1-alkenes as feed stocks, other lower olefins such as 2-butene or isobutylene, are readily employed as starting materials due to rapid isomerization over the acidic zeolite catalyst. Other mixed olefin rich streams can also be employed such as FCC off gas or Fischer Tropsch products. At conditions chosen to maximize heavy distillate and lubricant range products ($C_{20}+$) the raw aliphatic product is essentially mono-olefinic. Overall branching is not extensive, with most branches being methyl at about one branch per five or more atoms.

The viscosity index of a hydrocarbon lube oil is related to its molecular conformation. Extensive branching in a molecule usually results in a low viscosity index. It is believed that two modes of oligomerization/polymerization of olefins can take place over acidic zeolites such as HZSM-5. One reaction sequence takes place at shape constrained Bronsted acid sites inside the channels or pores, producing essentially linear materials. The other reaction sequence occurs on the outer surface, producing highly branched material. By decreasing the surface acid activity (surface $\alpha-$ value) of such zeolites, fewer highly branched products with low VI are obtained. Thus, U.S. Pat. No. 4,520,221 is concerned with the conversion of olefins to a 650° F.+ lube fraction by contacting the olefins over ZSM-5 or related catalyst at elevated temperatures and pressures wherein the catalyst is treated with a bulky alkylpyridine or other basic compound whereby the surface activity or acidity of the catalyst is removed or substantially eliminated.

Also, U.S. Pat. No. 4,547,613 discloses forming a lube oil by contacting olefins with ZSM-5 or related zeolite which has been conditioned by previous contact with a light olefin.

Other patents which disclose the conversion of olefins over zeolites such as ZSM-5 in order to produce higher boiling products such as 650° F.+ lube fractions include U.S. Pat. No. 4,517,399 which discloses contacting the olefins with ZSM-5 or related zeolite having a crystalline size greater than 2 microns; U.S. Pat. No. 4,126,644 which discloses the conversion of a $C_5$–400° F. liquid fraction from a Fischer-Tropsch synthesis, predominately $C_5$–$C_{10}$ olefins; and U.S. Pat. No. 3,322,848 which is directed towards the manufacture of high VI, low pour point lube oils from $C_{10}$–$C_{18}$ normal alpha olefins by processing over crystalline aluminosilicates other than those related to ZSM-5.

Another catalyst found useful in forming lubricants from the polymerization of olefins having between 5 and about 14 carbon atoms per molecule is ditertiary alkyl peroxide catalyst such as disclosed in U.S. Pat. No. 2,937,129.

Commonly assigned U.S. Ser. No. 709,143, filed Mar. 7, 1985, discloses a two stage olefin to lube conversion process wherein a lower olefin feed is oligomerized in a primary stage with a medium pore shape-selective siliceous zeolite catalyst having acid cracking activity, and constraint index of about 1 to 12 and wherein the zeolite surface is rendered substantially inactive for acidic reactions by chemisorption of a surface deactivating agent; and at least a portion of the primary stage effluent is converted in a secondary reactor stage with an acid catalyst ($BF_3$) to produce a high viscosity index lubricant range hydrocarbon.

One limitation of olefin oligomerization such as the MOGD process for producing lubes has been that higher viscosity lubes are not easily obtainable. A primary object of the present invention is to produce high viscosity lubes which have a low pour point and high viscosity index.

SUMMARY OF THE INVENTION

A multi-stage process has been devised for converting a feedstock comprising lower olefins to form higher hydrocarbons, particularly lubricants. A multi-stage process is provided for producing hydrocarbons by oligomerizing lower olefin feed at moderate temperature and elevated pressure which comprises contacting the lower olefin in a first reactor stage under oligomerization conditions with a medium pore siliceous zeolite catalyst having acid cracking activity, and a constraint index of about 1 to 12. After separating the first stage effluent to obtain a heavy fraction rich in substantially linear $C_{10}+$ intermediate olefins (330° F.+), the process is completed by contacting the heavy fraction in a second reactor stage with a ditertiary alkyl peroxide catalyst to upgrade the heavy fraction to a high viscosity index lubricant range hydrocarbon. This technique is advantageous for producing high viscosity $C_{20}+$ heavy hydrocarbons comprising lubricant range compounds (650° F.+) having viscosity indices and pour points about the same as those obtained in MOGD lube oils of lower viscosity.

DETAILED DESCRIPTION OF THE INVENTION

Lube range materials are obtained in accordance with the present invention in a two-stage process. Generally the first stage involves oligomerization of an inexpensive lower olefin of, e.g., propylene at moderate temperature over a shape selective crystalline aluminosilicate zeolite. The second stage involves further oligomerization/interpolymerization of the product (or a fraction of the product) from the first stage over a second and different catalyst at about 100°–200° C.

In the first stage of the process of the present invention, light olefins, e.g., $C_2$–$C_6$, are converted to distillate range boiling hydrocarbons by the MOGD process.

The oligomerization catalyst preferred for use in MOGD include the medium pore (i.e., about 5–7 angstroms) shape selective crystalline aluminosilicate zeolites having a silica to alumina ratio of at least 12, a constraint index of about 1–12 and acid cracking activity of about 50–200. Representative of the shape selective zeolites are ZSM-5, ZSM-11, ZSM-12, ZSM-22, ZSM-23, ZSM-35, ZSM-38, and ZSM-48. ZSM-5 is disclosed in U.S. Pat. No. 3,702,886 and U.S. Pat. No. Re. 29,948. Other suitable zeolites are disclosed in U.S. Pat. Nos. 3,709,979 (ZSM-11); 3,832,449 (ZSM-12); 4,076,979; 4,076,842 (ZSM-23); 4,016,245 (ZSM-35); 4,046,339 (ZSM-38); and 4,375,573 (ZSM-48) The disclosures of these patents are incorporated herein by reference.

A further useful catalyst is a medium pore shape selective crystalline aluminosilicate zeolite as described above containing at least one Group VIII metal, for example Ni-ZSM-5. This catalyst has been shown to convert ethylene at moderate temperatures and is disclosed in a copending U.S. patent application Ser. No. 775,906, filed Sept. 13, 1985.

Similarly, U.S. Pat. Nos. 4,542,251 and 4,517,396 disclose oligomerizing olefins over siliceous crystalline molecular sieve catalysts which contain nickel.

The catalyst for oligomerization of the olefinic feed can be composited with a suitable binder such as alumina and shaped in the form of cylindrical extrudates of about 1–5 millimeters diameter for use in fixed bed operation or particle size for use in fluid bed operation. Other pentasil catalysts which may be employed for converting lower olefins include a variety of medium pore (~5 to 9A) siliceous materials such as borosilicates, ferrosilicates, and/or aluminosilicates disclosed in U.S. Pat. Nos. 4,414,423; 4,417,086; and 4,517,396, incorporated herein by reference.

To reduce excessive branching in the lube molecule catalysts of low surface activity can be used. Such low surface active catalysts can be obtained by using medium pore zeolites of small crystal size that have been deactivated by basic compounds, examples of which are amines, phosphines, phenols, polynuclear hydrocarbons, cationic dyes and others. These compounds all must have a minimum cross section diameter of 5 Å or greater. Examples of suitable amines include monoamines, diamines, triamines, aliphatic and aromatic cyclic amines and heterocyclic amines, porphines, phthalocyanines, 1,10-phenanthroline, 4,7-diphenyl-1, 10-phenanthroline, 3,4,7,8-tetramethyl-1, 10-phenanthroline, 5,6-benzoquinoline, 2,2':6',2''-terpyridine, 2,4,6-tri(2-pyridyl)-S-triazine and 2,3-cyclododecenopyridine. Examples of phosphines include triphenylphosphine and 1,2-bis(diphenylphosphine)ethane. Suitable phenols are, for example, di-t-butylphenol, alkylated naphthol and 2,4,6-trimethylphenol. Polynuclear hydrocarbons include substances such as pyrene and phenanthrene. Cationic dyes include thionine, methylene blue and triphenylmethane dyes, such as malachite green and crystal violet. Another surface modification technique is deactivation by treating with metal compounds. Suitable metal compounds are magnesium acetate, metal-porphines, such a hemin or iron (III)) porphine chloride, cobalticinium chloride $(C_5H_5)_2CoCl$, and titanocene dichloride (biscyclopentadienyl titanium dichloride), large complex cations such as $[Co(NH_2R)_6]^{2+}$, where $R=H$, alkyl, $[Pt(NH_2R)_4]^{2+}$, where $R=$alkyl, $[co(en)_3]^{3+}$ where en=ethylenediamine, manganese (III) meso-tetraphenylporphine.

The catalysts may be treated with organic silicon compounds, as described in U.S. Pat. Nos. 4,100,215 and 4,002,697 to impart the desired degree of surface deactivation while being essentially free of carbonaceous deposits. Such treatment involves contacting the catalyst with a silane surface modifying agent capable of deactivating catalytic (acidic) sites located on the external surface of the zeolite by chemisorption. Those amines with an effective cross section larger than about 5 Angstroms are suitable especially substituted quinolines, heterocyclic amines and alkyl-substituted pyridines such as 2,4 or 2,-di-alkyl pyridines. Preferred are bulky, sterically-hindered di-ortho-alkyl pyridines, such as 2,6-di-tertiary-butylpyridine. The lower molecular weight $C_6-C_{20}$ intermediate materials formed over the modified catalysts are relatively linear olefins.

The general operating parameters for first stage MOGD in the process of the present invention can be defined by stating that the process carried out at pressures from about 100-2000 psig, at temperatures ranging from about 350°–700° F., and at a space velocities of 0.2-10 LHSV. It is to be immediately understood that the above recitation of ranges of pressure, space velocity, and temperature is not intended to mean that all operations within the above set forth limits will result in producing the desired results of the invention. On the contrary, what is meant by the above limits concerning temperature, pressure, and space velocity is best expressed in a negative way. In other words operations outside the ranges specifically set forth will not result in the improved process of this invention. It is well known in the art that there is a correlation between temperature, pressure, and space velocity with respect to the severity of a given chemical reaction. Quite simply put, the instant invention is concerned with the first stage oligomerization of a light olefinic stream to gasoline and distillate fuel range products.

In particular, the first stage MOGD is operated to obtain a greater proportion of distillate fuels, i.e., a $C_{10}+$ fraction boiling at 330° F. and above. Thus, the MOGD reaction is run at a moderate temperature of 375°–600° F. and relatively high pressure of about 400-2000 psig. The MOGD reactor can be fixed, moving or fluidized bed.

The effluent mixture from the first stage MOGD is separated into a high boiling product as a liquid rich in $C_{10}+$ hydrocarbons, and a vaporized volatile component including light gas and lower hydrocarbons, such as $C_1$ to $C_9$ aliphatics. The MOGD C10+ liquids are then converted to high viscosity index, low pour point lubes by conversion over a ditertiary alkyl peroxide catalyst.

In general, the synthetic lubricants are produced in the second stage by contacting in a reaction zone, at a temperature varying between about 100° C. and about 200° C., the MOGD $C_{10}+$ liquids with a ditertiary-alkyl peroxide catalyst.

The second stage catalyst used to produce the polymerized olefin synthetic lubricants of this invention are the ditertiary-alkyl peroxides. These peroxides can be represented by the formula, ROOR', wherein R and R' are like, or dissimilar, tertiary alkyl radicals. In preferred practice the tertiary alkyl radicals are lower tertiary alkyl radicals. Non-limiting examples of the catalyst are ditertiary-butyl peroxide, ditertiary-amyl peroxide, and tertiary-butyl tertiary-amyl peroxide.

The amount of peroxide catalyst employed in the process of this invention is determinative of the viscosity of the polyolefin synthetic lubricant product. In general, the more viscous lubricants are obtained when larger amounts of catalyst are used. The amount of ditertiary-alkyl peroxide catalyst employed will vary between about 0.01 and about 0.3 mole per mole of MOGD liquid reactant.

The ditertiary-alkyl peroxide catalyst can be added to the first stage MOGD reactant in a single addition. It is preferred, however, to add the catalyst in two or more portions at intervals of several minutes to several hours. A feasible procedure is to add the catalyst gradually to the reaction mixture throughout the course of the reaction.

The temperature employed in the second stage process of this invention is the activation temperature of the catalyst. The ditertiary-alkyl peroxides are activated at temperatures varying between about 100° C. and about 200° C., depending upon the particular peroxide selected. The pressure employed depends upon the temperature used and upon the reactant. Ordinarily, a pressure sufficient to maintain the reactants substantially in the liquid phase is sufficient. The time of reaction depends, of course, upon the temperature employed, the nature of the reactants, and to some extent the pressure. In general, the higher the reaction temperature, the shorter the reaction time required. The criterion used is the time required, at a given temperature, to effect condensation and to assure substantially complete utilization of the catalyst. In general, the time of reaction will vary between about one hour and about 6 hours.

At the temperatures required for the second stage conversion of this invention, some of the ditertiary-alkyl peroxide catalysts together with alcohol may tend to distill from the reaction zone. This material can be gathered in a suitable trap or receiver and recycled to the reaction zone. It is preferable, but not necessary, to wash the material with the water to remove alcohol prior to recycling.

Advantageously, the second stage effluent liquid stream is fractionated to provide a raw product stream comprising a major amount of $C_{10}-C_{20}$ distillate and $C_{20}-C_{60}$ aliphatic hydrocarbons. This raw olefinic product may then be hydrotreated in a separate process step to provide a paraffinic lubricant and/or heavy distillate product. Details of a mild hydrogenation treatment may be obtained from U.S. Pat. No. 4,211,640, incorporated by reference, typically using Co or Ni with W/Mo and/or noble metals. The hydrotreated stream may be further fractionated to yield refined high grade lubricants of outstanding quality.

As has been mentioned hereinbefore, the 650° F.+ product of this invention is a lube oil of outstanding properties. The lubricants have a viscosity as high as 1300 Saybolt Universal Second (SUS) at 100° F. and 86 SUS at 210° F. Higher viscosities are obtained by increasing the amount of peroxide. Viscosity indices and pour points are about the same as those obtained in MOGD-L when compared at lower viscosities.

The following specific working examples are for the purpose of illustrating the lube oils of this invention and the manner of producing them. It will be understood that this invention is not to be limited to the specific olefins and catalyst used in the examples, or to the particular operations and manipulations involved.

EXAMPLE 1

The MOGD liquid was prepared by processing a mixed olefin of propane/propylene/butane/butylene over HZSM-5 extrudate catalyst in a pilot unit run at 1 LHSV (olefin), 800 psig, 2/1 recycle of 70°–450° F. product/fresh olefin, 480°–489° F. over a 12–22 day period. The 330° F.+ product, 84 wt. % yield based on fresh feed, had the following properties:

| Gravity, °API | 44.7 |
|---|---|
| Specific | 0.8031 |
| Hydrogen, wt. % | 14.32 |
| Bromine No. | 60.5 |
| Aniline Point | 175 |
| Distillation, °F., ASTM | D-2887 |
| 0.5% | 315 |
| 10 | 438 |
| 20 | 462 |
| 30 | 480 |
| 40 | 498 |
| 50 | 519 |
| 60 | 544 |
| 70 | 575 |
| 80 | 612 |
| 90 | 664 |
| 95 | 704 |
| 99.5 | 807 |

300 g of the liquid was placed in a 1 liter round bottom flask equipped with a stirrer, thermometer, water condenser, and dropping burette. The flask was heated to 150° C., and 12 g (15.6 ml) ditertiary butyl peroxide (DTBP) added dropwise from the burette over a 1 hour period. The temperature was held at 150° C. for an additional 3 hours, then raised to 186° C. in the next 2 hours. The contents were then cooled to room temperature and were analyzed as follows:

| Gravity, °API | 43.7 |
|---|---|
| Specific | 0.8076 |
| Distillation, °F., | |
| 1% | 110 |
| 10 | 426 |
| 20 | 459 |
| 30 | 481 |
| 40 | 504 |
| 50 | 531 |
| 60 | 567 |
| 70 | 611 |
| 80 | 674 |
| 90 | 770 |
| 95 | 833 |
| 99.5 | 949 |

The liquid product was distilled first at atmospheric pressure to remove lighter boiling material, then under reduced pressure to separate a 21 wt. % ~650° F.+ bottoms fraction having the following properties:

| Gravity, °API | 35.3 |
|---|---|
| Specific | 0.8483 |
| Pour Point, °F. | <−65 |
| KV @ 40° C., cs | 35.90 |
| KV @ 100° C., cs | 5.47 |
| SUS @ 100° F. | 186 |
| Viscosity Index | 81.6 |

EXAMPLE 2

The MOGD liquid of Example 1 was distilled to give 89 wt. % overhead boiling below 650° F., and 11 wt. % 650° F.+ bottoms having the following properties:

| Gravity, °API | 38.2 |
|---|---|
| Specific | 0.8338 |
| Pour Point, °F. | −60 |
| KV @ 40° C., cs | 14.29 |
| KV @ 100° C., cs | 3.225 |
| SUS @ 100° F. | 79 |
| Viscosity Index | 84.0 |

This bottoms material was a part of the charge to Example 1. However, it can be seen that the DTBP polymerized product of Example 1 has about the same viscosity index and pour point, and is much more viscous (186 vs 79 SUS @ 100° F.).

EXAMPLE 3

300 g of the overhead material boiling below 650° F. from Example 2 was polymerized with DTBP in the same manner as in Example 1, except that the procedure was repeated twice more, using a total of 36 g (46.8 ml) DTBP. The liquid product was analyzed as follows:

| Gravity, °API | 41.7 |
|---|---|
| Specific | 0.8170 |
| Distillation, °F., | |
| 1% | 122 |
| 10 | 439 |
| 20 | 471 |
| 30 | 497 |
| 40 | 527 |
| 50 | 571 |
| 60 | 625 |
| 70 | 708 |
| 80 | 778 |
| 90 | 852 |
| 95 | 903 |
| 99.5 | 989 |

The liquid product was distilled yielding a 40 wt. % 650° F.+ bottoms lube having the following properties.

| Gravity, °API | 34.8 |
|---|---|
| Specific | 0.8509 |
| Pour Point, °F. | −55 |
| KV @ 40° C,. cs | 48.79 |
| KV @ 100° C., cs | 6.51 |
| SUS @ 100° F. | 253 |
| Viscosity Index | 77.1 |

The ~650° F.+ bottoms lube was distilled further at 0.03 mm pressure, to give 51% ~800° F.+ bottoms (20 wt. % based on original charge) having the following properties:

| | |
|---|---|
| Gravity, °API | 32.1 |
| Specific | 0.8649 |
| Pour Point, °F. | +15 |
| KV @ 40° C., cs | 243.4 |
| KV @ 100° C., cs | 16.59 |
| SUS @ 100° F. | 1309* |
| Viscosity Index | 61.3 |

*86.6 SUS @ 210° F.

This Example demonstrates that very viscous lubes can be produced by increasing the amount of DTBP and distilling beyond the normal 650° F. cut point.

EXAMPLE 4

The liquid charge for this Example was prepared by processing a propylene/butylene stream (propane/-propylene/butane/butylene, 10.5/26.8/27/35.1) over HZSM-5 extrudate in a pilot plant run at ~0.5 LHSV, 1500 psig, with recycle of 70 to ~600° F. liquid and temperature 400°–450° F. The liquid product was distilled to give 57 wt. % 330°–650° F. overhead, and 39 wt. % 650° F.+ MOGD lube product having the following properties:

| | |
|---|---|
| Gravity, °API | 35.4 |
| Specific | 0.8478 |
| Pour Point, °F. | <−65 |
| KV @ 40° C., cs | 17.53 |
| KV @ 100° C., cs | 3.615 |
| SUS @ 100° F. | 94 |
| Viscosity Index | 78.7 |

The 300°–650° F. liquid had the following properties:

| | |
|---|---|
| Gravity, °API | 42.2 |
| Specific | 0.8146 |
| Bromine No. | 46.2 |
| Aniline Point | 171 |
| Distillation, °F., | |
| 0.5% | 284 |
| 5 | 363 |
| 10 | 392 |
| 20 | 445 |
| 30 | 494 |
| 40 | 542 |
| 50 | 574 |
| 60 | 593 |
| 70 | 609 |
| 80 | 623 |
| 90 | 639 |
| 95 | 649 |
| 95.5 | 695 |

300 g of this liquid was polymerized with DTBP in the same manner as in Example 3, and then distilled to give 41 wt. % 650° F.+ bottoms product having the following properties:

| | |
|---|---|
| Gravity, °API | 32.1 |
| Specific | 0.8649 |
| Pour Point, °F. | −45 |
| KV @ 40° C., cs | 64.05 |
| KV @ 100° C., cs | 7.465 |
| SUS @ 100° F. | 335 |
| Viscosity Index | 69.7 |

EXAMPLE 5

The 650° F.+ lube product from Example 4 was hydrogenated using a nickel catalyst. 75 g of the lube was diluted with 200 ml cyclohexane and charged along with 2.3 g of the catalyst to a 2 liter stirring autoclave. The autoclave was purged three times with 500 psig nitrogen, then three times with hydrogen, then finally pressured to 400 psig hydrogen and heated at 350° F. for 1½ hours. The contents were cooled, the cyclohexane distilled off, leaving a bottoms with the following properties:

| | |
|---|---|
| Gravity, °API | 32.9 |
| Specific | 0.8607 |
| Pour Point, °F. | −50 |
| KV @ 40° C., cs | 63.69 |
| KV @ 100° C., cs | 7.38 |
| SUS @ 100° F. | 333 |
| Viscosity Index | 67.2 |

The Example shows that hydrogenation has little effect on the physical properties of the lube.

EXAMPLE 6

The liquid charge for this Example was prepared by processing a propylene/butylene stream over a 2,6 ditertiary butyl pyridine pretreated HZSM-5 catalyst. The pretreating was by wetting the catalyst with a mixture of 2,6 DTBP in n-hexane followed by evaporation of the hexane. Reaction conditions were 1000 psig, 0.5 LHSV (olefin), ~400° F. over a five day period. The liquid product was distilled to give 55.8 wt. % 330°–650° F. overhead, and 10.7 wt. % 650° F.+ lube product having the following properties:

| | |
|---|---|
| Gravity, °API | 34.3 |
| Specific | 0.8534 |
| Pour Point, °F. | <0 |
| KV @ 40° C., cs | 19.25 |
| KV @ 100° C., cs | 4.02 |
| SUS @ 100° F. | 102 |
| Viscosity Index | 125.0 |

250 g of the 330°–650° F. overhead liquid was polymerized with DTBP (30 g, 39 ml) in the same manner as in Example 3, and then distilled to give 24 wt. % 650° F.+ bottoms product having the following properties:

| | |
|---|---|
| Gravity, °API | 36.0 |
| Specific | 0.8448 |
| Pour Point, °F. | <−65 |
| KV @ 40° C., cs | 40.83 |
| KV @ 100° C., cs | 5.98 |
| SUS @ 100° F. | 211 |
| Viscosity Index | 85.6 |

The viscosity index is higher than that of the 650° F.+ lubes produced with DTBP in the previous examples. This is believed to be due to a more linear mixture of olefinic molecules in the 330°–650° F. charge, compared to the previous examples where secondary non-shape selective surface reactions degrade (isomerize and crack) the primary olefin mixture.

EXAMPLE 7

Isomers of $C_8$ olefins were oligomerized in the presence of ditertiary butyl peroxide catalyst. The reactions were done at 150° C., using 25.8 wt. % peroxide on olefin.

| Olefin Charge | Octene-1 | Octene-2 | 2-Ethyl-Hexene-1 |
|---|---|---|---|
| Oil Yield, Wt. % | 20.9 | 2.6 | 1.1 |
| Pour Point, °F. | <−30 | <−30 | −15 |
| K.V. @ 100° F., cs | 111.9 | 55.34 | 190.4 |
| K.V. @ 210° F., cs | 13.53 | 7.06 | 11.95 |
| Viscosity Index | 120 | 91 | 29 |

The data show that both an internal double bond and ethyl branching next to a terminal bond limit lube yields severely, and in addition the ethyl branching decreases viscosity index markedly.

EXAMPLE 8

The charge stock in this work was a blend of equal weights of Shell Chemical straight chain 1-olefins, $C_{10}$, $C_{12}$, $C_{14}$, $C_{16}$, $C_{18}$, $C_{20}$. The boiling range of the blend covered essentially the same 330°–650° F. range of Example 3. Results are as follows:

| Run No. | 1 | 2 |
|---|---|---|
| Peroxide, wt. % on olefin | 4[1] | 12[2] |
| 650° F. + Lube yield, wt. % | 60.6 | 94.7 |
| Gravity, °API | 37.3 | 34.2 |
| Specific | 0.8383 | 0.8545 |
| Pour Point, °F. | +50 | — |
| K.V. @ 40° C., cs | 66.92 | 476.0 |
| K.V. @ 100° C., cs | 12.40 | 54.06 |
| SUS @ 100° F. | 338 | 2460 |
| SUS @ 210° F. | 69 | 260 |
| Viscosity Index | 187 | 180 |

[1] 300 g olefin blend, 12 g DTBP added as in Example 1
[2] 300 g olefin blend, 36 g DTBP added as in Example 3

Compared to the 330°–650° F. MOGD liquid charge of Example 3, the 1-olefin blend gives a much higher yield of very viscous, high viscosity index lube, but also a much higher pour point, too high for usage as a lubricant.

What is claimed is:

1. A multi-stage process for producing lubricant range hydrocarbons by oligomerizing a low olefin feedstock which comprises contacting said lower olefin feedstock in a first reactor stage under oligomerizing conditions with a medium pore shape-selective siliceous zeolite catalyst and contacting at least a portion of the first stage effluent in a second reactor stage with a ditertiary alkyl peroxide catalyst to produce a high viscosity lubricant range hydrocarbon.

2. The process of claim 1 wherein said first stage catalyst is a crystalline aluminosilicate zeolite having a constraint index of about 1 to 12.

3. The process of claim 2 wherein the surface of said zeolite is rendered substantially inactive for acid reactions by chemisorption of a surface deactivating agent.

4. The process of claim 3 wherein said surface deactivating agent is a dialkylpyridine.

5. The process of claim 1 including separating the effluent from the first stage to obtain a heavy fraction rich in $C_{10}+$ olefins and contacting said heavy fraction in said second stage with said second stage catalyst.

6. The process of claim 1 wherein said second stage is operated at a temperature of about 100°–200° C.

7. The process of claim 6 wherein said second stage catalyst is ditertiary butylperoxide.

8. The process of claim 1 wherein said first stage is operated at a temperature of about 375°–600° F. and at a pressure of about 400–2000 psig.

9. The process of claim 8 including separating the effluent from the first stage to obtain a heavy fraction rich in $C_{10}+$ olefins and contacting said heavy fraction in said second stage with said second stage catalyst.

10. The process of claim 9 wherein the lubricant range hydrocarbon has an initial boiling point of about 650° F.

11. The process of claim 1 wherein said first stage catalyst comprises ZSM-5.

12. The process of claim 1 wherein said lower olefin feedstock comprises a mixed stream of $C_2$–$C_6$ olefins.

13. The process of claim 8 wherein said second stage is operated at a temperature of about 100°–200° C.

14. The process of claim 13 wherein said second stage catalyst is ditertiary butylperoxide.

15. The process of claim 14 including separating the effluent from the first stage to obtain a heavy fraction rich in $C_{10}+$ olefins and contacting said heavy fraction in said second stage with said second stage catalyst.

* * * * *

UNITED STATES PATENT AND TRADEMARK OFFICE
CERTIFICATE OF CORRECTION

PATENT NO. : 4,618,737

DATED : October 21, 1986

INVENTOR(S) : Arthur W. Chester, William E. Garwood and Samuel A. Tabak

It is certified that error appears in the above-identified patent and that said Letters Patent is hereby corrected as shown below:

Col. 1, line 17, "heaver" should be --heavier--.

Col. 2, lines 13-14, "$\overset{H}{\underset{\parallel}{C}}$" should be --$\overset{H}{\underset{|}{C}}$--.

Col. 3, line 31, after "and" insert --a--.

Col. 5, line 35, after "process" insert --is--.

Col. 11, Claim 1, "low" should be --lower--. (line 42)

Signed and Sealed this

Sixth Day of January, 1987

Attest:

DONALD J. QUIGG

Attesting Officer

Commissioner of Patents and Trademarks